Figure 1:
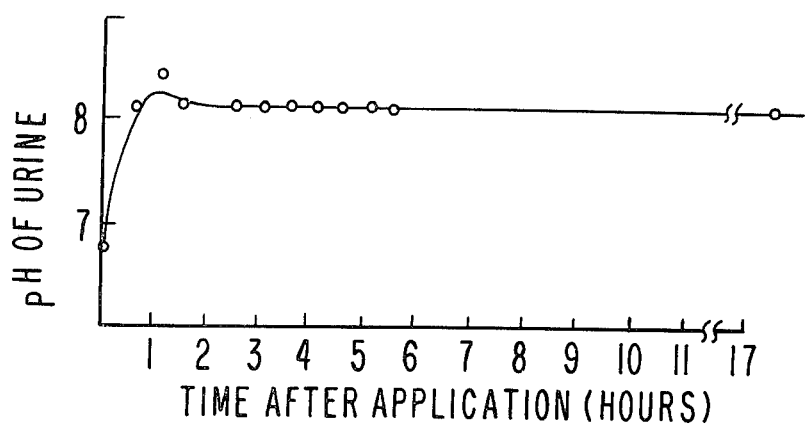

United States Patent [19]

Schmitt

[11] 4,122,158

[45] * Oct. 24, 1978

[54] TOPICAL THERAPEUTIC PREPARATIONS

[75] Inventor: Edward Emil Schmitt, Palo Alto, Calif.

[73] Assignee: Alza Corporation, Palo Alto, Calif.

[*] Notice: The portion of the term of this patent subsequent to Sep. 28, 1993, has been disclaimed.

[21] Appl. No.: 809,963

[22] Filed: Jun. 27, 1977

Related U.S. Application Data

[63] Continuation of Ser. No. 725,765, Sep. 23, 1976, abandoned, which is a continuation of Ser. No. 544,807, Jan. 28, 1975, Pat. No. 3,983,209.

[51] Int. Cl.$^2$ .................. A61K 9/70; A61K 31/765; A61K 31/77
[52] U.S. Cl. .................. 424/27; 424/28; 424/78; 424/94; 424/228; 424/229
[58] Field of Search .............. 424/78, 228, 229, 28, 424/27

[56] References Cited

U.S. PATENT DOCUMENTS 3,983,209   9/1976   Schmitt .................................. 424/78

OTHER PUBLICATIONS

The Merck Manual – 12th edition (1972) pp. 1492–1496.

*Primary Examiner*—Sam Rosen
*Attorney, Agent, or Firm*—Paul L. Sabatine; Thomas E. Ciotti; Edward L. Mandell

[57] ABSTRACT

A method is disclosed for treating the burned surface of an animal by administering to said surface a contact composition comprising a hydrophobic, bioerodible polymer containing an agent selected from the group consisting of antibacterial, antibiotic, antifungal, proteolytic enzyme and mixtures thereof, which composition when placed in contact with the burned surface maintains homeostasis including prevention of tissue dehydration and thermal loss, and as the polymer bioerodes over time, releases agent to produce a continuous chemoprophylatic or chemotherapeutic effect.

6 Claims, 3 Drawing Figures

TOPICAL THERAPEUTIC PREPARATIONS

CROSS-REFERENCE TO RELATED APPLICATIONS

This application is a continuation of Ser. No. 725,765, filed Sept. 23, 1976, now abandoned; which was a continuation of Ser. No. 544,807, filed Jan. 28, 1975, now U.S. Pat. No. 3,983,209.

BACKGROUND OF THE INVENTION

The present invention relates to a method for treating burns of mammals. More particularly, the invention pertains to a method for treating burns by applying topically to a burned surface a composition comprising an antibacterial, antibiotic, antifungal or proteolytic agent in a hydrophobic, bioerodible polymer of the formula:

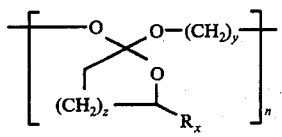

wherein x is 0 or 1 and when 1 R is a lower alkyl of 1 to 7 carbons such as methyl, ethyl, propyl and butyl, $y$ is 4 to 10, $z$ is 1 to 3 and $n$ is 10 to 1000, which polymer impedes the passage of water vapor and prevents excessive heat loss from the burned area and bioerodes over time concurrently with release of an effective amount of the agent for prophylaxis for controlling infection or for regulating wound healing.

There are many serious problems associated with the care and treatment of topical burns. For example, the problems include dehydration due to loss of skin vapor barrier capability, direct thermal loss through burned skin and underlying epithelial tissues, and evaporative heat loss by leakage of water vapor, all of which problems must be controlled to maintain body homeostasis. Additionally, eschar and necrotic tissue must be removed and burn wound sepsis due to bacterial colonization and fungal invasion must also be controlled for successful burn management.

Present attempts to prevent dehydration of, and thermal loss from, patients with major burn injuries consists in applying to the wound site biological dressings such as freeze-dried cadaver skin allografts commercially available as Synknit ®, pigskin Xenografts ®, amnion and fibrin films or synthetic dressings consisting of polymeric films of polyethylene, polyurethane or Teflon ®, or a composite of above-mentioned polymers commercially available as Epigard ® to cover denuded surfaces until they can be replaced with autografts. However, these dressings have inherent shortcomings which limit their use. For example, the natural materials are scarce and in heavy demand, they are protein in structure which can lead to rejection, they are susceptible to infection and they lack the ability to carry chemotherapeutic agents. Similarly, the synthetic materials lack the physical characteristics of naturally occurring skin and this severely restricts their use.

Present attempts to prevent bacterial and fungal proliferation or to control burn infection usually consist in applying to the burned area a cream containing an antibacterial, antibiotic or antifungal agent. While these creams are useful for their intended purpose, they are not entirely satisfactory because of certain inherent disadvantages. For example, the creams tend to run after they warm to physiological temperature and become unevenly distributed over the burned area. Also, the amount of agent made available by the cream varies over time. That is, the creams on application initially supply a large amount of agent that inhibits unwanted proliferation, followed by continuously decreasing amounts of agent that may not inhibit proliferation and lead to fatal invasive sepsis.

OBJECTS OF THE INVENTION

Accordingly, it is a primary object of this invention to provide a novel method for the management of burns that overcomes the difficulties and tribulations associated with the prior art.

Yet another object of the invention, is to provide a method for the treatment of burns which makes available a member selected from the group consisting of antibacterial, antibiotic, antifungal and proteolytic agents and mixtures thereof, to a burned surface at a continuous rate over a prolonged period of time.

Yet another object of the invention is to provide a method for treating burns comprising the step of applying to a burned site a chemoprophylaxis or chemotherapeutic agent dispersed in a hydrophobic polymer that releases the agent to the site simultaneously with erosion of the polymer.

Still a further object of the invention is to provide a method of treating burns in mammalians, including animals, by applying to the burned surface a therapeutic system comprising a hydrophobic polymer containing an agent useful in the management of burns that is released from the polymer in an effective amount to said animal afflicted with a burn.

Still a further object of the invention is to provide a method for maintaining body homeostasis in a burned animal by applying to the burned site a biologically acceptable hydrophobic polymer that covers the denuded site for maintaining said homeostasis.

Yet a further object of the invention is to provide a method for treating a burned surface to prevent loss of water vapor by applying to the surface a hydrophobic polymer possessing a vapor barrier capability.

Another object of the invention is to provide a method for substantially decreasing thermal loss from a burned surface by applying to the burned surface a hydrophobic polymer that acts as an impervious coating to impede the loss of heat.

Yet still another object of the invention is to provide a nonaqueous hydrophobic bioerodible polymeric carrier containing a proteolytic enzyme useful for debridement of eschar and necrotic tissues associated with burns.

Yet another object of the invention is to provide an improved therapy for burns comprising applying to the burned surface a hydrophobic polymer containing a proteolytic enzyme and at least one of an antibacterial, antibiotic or antifungal agent for application to the burned surface.

Other objects and advantages of this invention will become more apparent from the following detailed description, the examples, and the accompanying claims.

DESCRIPTION OF THE DISCLOSURE

In attaining the objects, features and advantages of the invention, it has now been found that an efficient and reliable method can be made available to the medical and veterinary professions for the management of burns which comprises applying to the burned site a hydrophobic bioerodible polymer containing an antibacterial, antibiotic, antifungal, proteolytic agent or other beneficial agent.

The agents suitable for the purpose of the invention are presently known agents, including the antibacterial agents such as sodium sulfacetamide, silver sulfadiazine, sulfadimethoxine, sulfaethidole ethiodic, sulfamethazine, aminosalicyclic acid, sulfamethizole, sulfamethoxazole, sulfapyridine, homosulfamilamide, sulfamylon acetate, sulfamylon hydrochloride, citylpyridinium chloride, silver nitrate, 5-chloro-3′-trifluoromethyl salicylanilide, 4-methylbenzimidazolone chlorhexidine and hexachlorophene. Antibiotics suitable for use herein include bacitracin, zinc bacitracin, chlortetracycline monohydrochloride, colistin sulfate, cycloserine, erythromycin, chloramphenicol, gentamicin sulfate, neomycin sulfate, polymyxin sulfate, ampicillin, sodium cephalothin, penicillin, and lincomycin. Representative antifungal agents include basic fuchsin, griseofulvin, nifuroxime, nystatin, sodium propionate, nitrofurantoin and sodium nitrofurantoin. Proteolytic enzymes useful for debridement of eschar and necrotic tissue to permit wound healing include papain, trypsin, collagenase, subitilisin, Ficin ®, pepsin, lysozyme, streptokinase, fibrinolysin, Pinguinain ®, Travase ®, and Bromelin ®. These enzymes are known to the art in U.S. Pat. Nos. 2,950,227 and in 3,002,891. The proteases are also described in Merck Index, page 164, 1968; *Physician Desk Reference*, pages 769 to 770, 1974; Ann. Surg., Vol. 134, pages 581 to 583, 1951; *J. Agr. U. of Puerto Rico*, Vol. 29, page 35, 1945; and Sci., Vol. 95, pages 48 to 49, 1942.

The polymers suitable for the purpose of the invention have the following general formula:

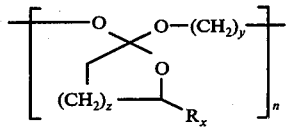

wherein $x$ is 0 or 1, and when 1 R is a lower alkyl of 1 to 7 carbons such as methyl, ethyl, propyl, isopropyl, butyl, hexyl, t-butyl and heptyl, $y$ is a positive whole number of 4 to 10, $z$ is a positive integer of 1 to 3, and $n$ is at least 10, generally 10 to 1000. The polymers embraced by the above formula are the invention of Nam S. Choi and Jorge Heller and they are not my invention. The polymers are disclosed and claimed by Choi and Heller in U.S. Pat. application Ser. No. 544,808 filed on Jan. 28, 1975 and further identified by attorney docket number Pm 5066. Both applications are assigned to ALZA Corporation of Palo Alto, Calif. 94304.

Broadly speaking, the practice of this invention is effected by dispensing or mixing about 0.001 to 30% by weight of the active agent into the polymer to prepare a therapeutic preparation suitable for topical application. The agent is added, mixed and dispersed throughout the polymer by conventional means. For example, a spatula, V-shaped blender, or three-roll mill can be used for this purpose. In use, the polymer containing the active ingredient is applied directly to the affected site for the management of burns.

Also, the agent-loaded polymer in another embodiment, is incorporated into an absorbent carrier and then applied to the burned surface while supported on the carrier. The carrier can be a fabric, or plastic fiber, a section of porous foamed rubber or a paper substrate. Carriers suitable for polymer drug impregnation include double knit polyesters, polyester or polyolefin fibers, cotton gauze, double selvage edged gauze, surgical linen, bleached cotton percale, synthetic hydrophobic polyamide textile materials and cellulosic fabrics. The fabric is impregnated with a polymer charged with active agent by first washing the fabric in hot water for 7 to 15 minutes, followed by pressing the fabric between paper towels to remove excess water, and then soaking the fabric in a boiling ethanol-water solution consisting of 3 parts of ethanol to 1 part of water for about 10 to 20 minutes with excess solution again removed by draining and pressing the fabric between towels. The fabric is dried in a forced air oven at 90° C. for one hour with complete drying in a vacuum oven for one hour at 80° C. The clean, dry fabric is then cut into various shapes, such as a circle with a 60 mm diameter or 4 inch squares, and charged with active agent. For example, a circular section of double knit polyester fabric is charged with 4 grams of poly(2,2-dioxohexamethylene tetrahydrofuran) containing 0.1 to 30%, usually 2, 4, 5, 10 or 15%, of α-amino-p-toluene sulfonamide by working the polymer-agent into the fabric with a laboratory spatula. Similarly, the hydrophobic polymer can be charged with other agents such as 1 to 1½% silver nitrate in poly(2,2-dioxohexamethylene tetrahydrofuran), from 0.001 to 2% by weight of collagenase mixed with 1 to 1½% by weight of silver nitrate in poly(2,2-dioxohexamethylene tetrahydrofuran), and 1 g of poly(2,2-dioxohexamethylene tetrahydrofuran) containing $82 \times 10^3$ casein units of a protease such as streptokinase, or sutilains. Polyester pads or fibers are also impregnated or coated by passing them through a three-roll mill in the presence of polymer-agent combination.

In order to further illustrate the practice of the invention, the following examples are given.

Fifteen adult Sprague-Dawley Holtzmann strain rats stabilized on standard laboratory rat chow ad water and libitum were used in this study. The rat's backs were shaven over an area of about 30% of their body surface and the rats anesthetized with intraperitoneal Nembutal ®pentobarbital sodium. Then, each rat was fitted with a protective template and their exposed backs placed in contact with boiling water for 10 seconds, according to the procedure described in Annals of Surg., Vol. 160, pages 297 to 305, 1964, and in J. Surg. Res., Vol. 4, pages 200 to 219, 1964. This procedure produces a uniform full-thickness burn with average major and minor axes of 9.3 cm ± 0.2 cm and 5.8 ± 0.2 cm, as determined by the equation and standard parameters given in *Texas Reports on Biology and Medicine*, Vol. 20, page 12, 1962. Next, a circular cotton gauze pad was placed over the burned surface and seeded with one milliliter of an aqueous broth of *Pseudomonas aeruginosa* containing $1 \times 10^8$ organisms. The bacterial suspension was evenly applied over the gauze surface. The animals were wrapped with a sterile bandage and placed aside for 24 hours in a controlled temperature room. Then, the animals were divided into three groups, their bandages removed, and a new 10 cm diameter dressing of one of the following applied to the afflicted burned surface of each rat in the group: (a) to the control group was applied a 1 mm thick sheet of washed double knit fabric, (b) to another group was applied a 1 mm thick sheet of polyester double knit fabric impregnated with the prior art preparation Sulfamylon ® consisting of 4-homosulfanilamide dispersed in cetyl alcohol, stearyl alcohol, spermaceti, polyoxyl 40 stearate, polyoxyl 8 stearate, glycine and water, and (c) to the third group was applied the burn therapy of the invention consisting of a 1 mm thick sheet of polyester double knit fabric impregnated with a mixture of 10% 4-homosulfanilamide homogenously dispersed in 90% poly(2,2-dioxohexamethylene tetrahydrofuran). The animals were kept in three groups for the remainder of the experiment with each animal given a new dressing ever 24 hours.

The results of the study showed in the control group of rats, which received the plain polyester fabric, one died 9 days post-burn and another died 11 days post-burn. An autopsy indicated the rats died of systemic pathogenic Pseudonomas aeruginosa infection. In the group of rats that received polyester impregnated with the prior art preparation containing 4-homosulfanilamide acetate, one rat died 11 days post-burn with death due to Pseudonomas aeruginosa. No animals died in the group receiving the fabric impregnated with the burn therapy of the invention comprising 4-homosulfanilamide in poly(2,2-dioxohexamethylene tetrahydrofuran). After 14 days post-burn, the rats were sacrificed, autopsied, and their eschar, liver, spleen and lungs assayed for Pseudomonas aeruginosa. Homogenates of the biopsied eschar were assayed for bacterial count and smears of the sliced surfaces of their organs, were incubated on trypticase soy agar plates at 37° C. for 48 hours and macroscopically examined for the presence of yellow-green pyocyanin pigment and for oxidase positive reactions. The latter two tests were uniquely diagnostic of the presence of Pseudomonas aeruginosa. The results of these studies are presented in the accompanying tables. Table 1 lists the number of deaths, survivals, total population count in the biopsied eschar and number of times Pseudomonas was detected in the organs of each group. Population counts were made by standard methods as described in *Microbiological Methods*, by Collins, C. H., pages 146 to 148, 1967, published by Plenum Press. Table 2 summarizes the qualitative tests for the presence of Pseudomonas in the internal organs. The oxidase test used for detecting the presence of Pseudomonas is reported in Nature, Vol. 178, page 703, 1956, and in *Diagnostic Microbiology*, by Bailey, W. R., and Scott, E. G., pages 130, 401, and 402, 1974, published by C. V. Mosby Company. The test for detecting Pseudomonas by pyocyanin dye is reported in the latter reference on page 163.

Table 1

|  | Plain Fabric | Sulfamylon° impregnated Fabric | Polymer-4-homo-sulfanil-amide impregnated Fabric |
|---|---|---|---|
| Number of deaths by Pseudomonas | 2 | 1 | 0 |
| Number of animals surviving experiment | 3 | 4 | 5 |
| Bacterial count of Pseudomonas in burned tissue per gram | 4.5 × 10⁸ | 9 × 10⁷ | 7 × 10⁶ |
| Number of positive indicators of Pseudomonas in autopsied organs | 27 | 19 | 0 |
| Number of negative indicators of Pseudomonas in autopsied organs | 3 | 11 | 30 |

Table 2

| Group | Animal | Lung O P | Spleen O P | Liver O P |
|---|---|---|---|---|
| C | 1 | − − | + + | + + |
|  | 6 | + − | + + | + + |
|  | 7 | + + | + + | + + |
|  | 8 | + + | + + | + + |
|  | 10 | + + | + + | + + |
| PA | 2 | + + | + + | + + |
|  | 3 | − − | − − | − − |
|  | 4 | + − | + + | + + |
|  | 5 | − − | + + | + + |
|  | 13 | − − | + + | + + |
| BT | 9 | − − | − − | − − |
|  | 11 | − − | − − | − − |
|  | 12 | − − | − − | − − |
|  | 14 | − − | − − | − − |
|  | 15 | − − | − − | − − |

In Table 2, the presence of *Pseudomonas* in internal organs is indicated for oxidase by (O) and green pyocyanin pigment by (P) (+ = present; − = absent); and wherein C is for control, PA is for prior art, BT is for burn therapy of the invention.

Figure 2:
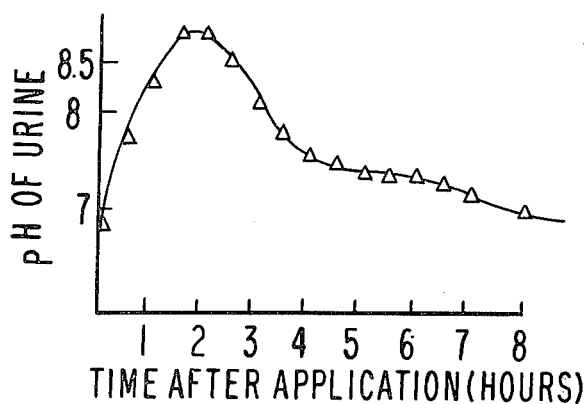
Figure 3:
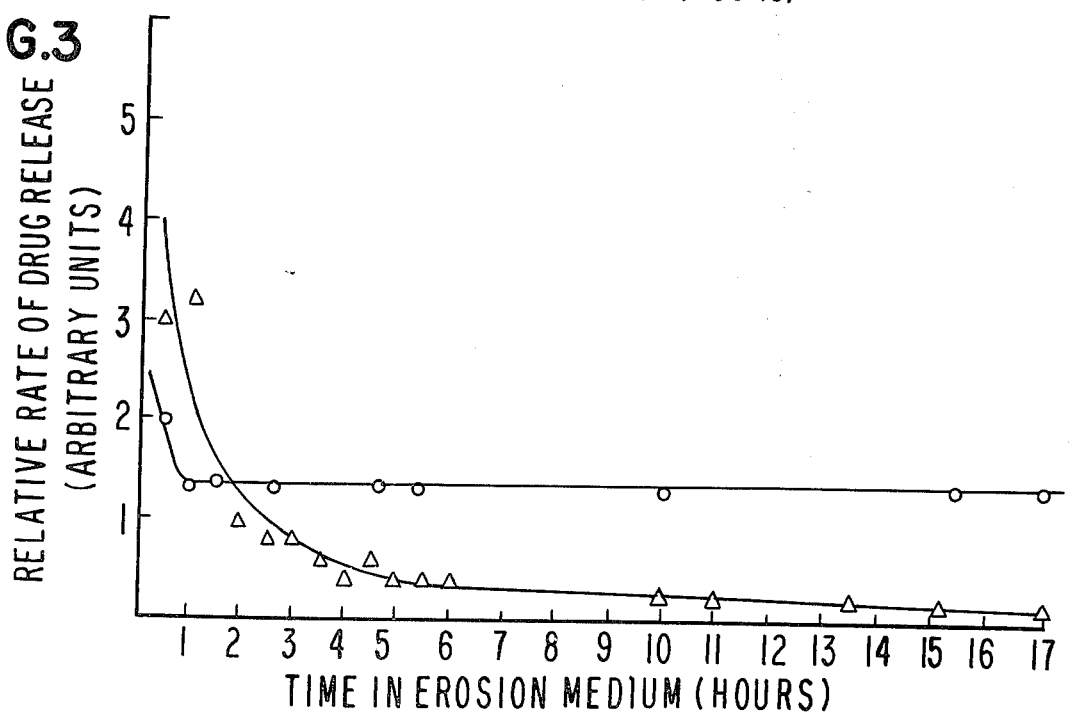

Demonstration of the zero order systemic absorption rate of drug release from a 30% suspension of 4-homosulfanilamide in poly(2,2-dioxohexamethylene tetrahydrofuran) for application as a chemoprophylactic or chemotherapeutic agent is illustrated in FIG. 1. In FIG. 1, the polymer-drug was applied as a 2 mm coat to 45% deskinned rats. The basic urine is a measure of anticarbonic anhydrase effect of the active agent. Each gram of polymer contained 300 mg of free base, and the denuded area covered was approximately 41 cm². In contrast, the same agent in the form of the acetate salt released from the prior art cream base applied to an area of 41 cm² in a 2 mm thick coat, gave the response seen in FIG. 2. In FIG. 3, the controlled and continuous release of 4-homosulfanilamide, illustrated by circles, from the polymers used herein and from the cream, illustrated by triangles, is set forth to further illustrate the added medical value of the invention.

The polymer-agent composition and the polymer-agent-fabric composite used according to the mode and manner of the invention, adhere to wounded surfaces with good tackiness that permits better dressing technique. The compositions comprising polymer and agent and the composite comprising polymer, agent and fabric, remain on the surface where they are placed and concurrently prevent transpiration and retard body heat loss, essentially free of non-toxic effects.

As will be apparent to those skilled in the art in the light of the accompanying disclosure, many alterations, substitutions and modifications are possible in the practice of the invention without departing from the spirit or scope thereof.

I claim:

1. A therapeutic preparation for topical application comprising an absorbent carrier containing a composition, which composition comprises an effective amount of a polymer of the general formula:

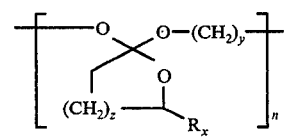

wherein R is a lower alkyl of 1 to 7 carbons, $x$ is 0 or 1, $y$ is 4 to 10, $z$ is 1 to 3 and $n$ is 10 to 1000; said polymer having mixed therein from 0.001 to 30% of a chemotherapeutic selected from the group consisting of sodium sulfacetamide, silver sulfadiazine, sulfadimethoxine, sulfaethidole, sulfamethazine, sulfamethizole, sulfamethoxazole, sulfapyridine, homosulfamilamide, sulfamylon acetate, sulfamylon hydrochloride, aminosalicyclic acid, cetylpyridinium chloride, silver nitrate, 5-chloro-3-tri-fluoromethyl salicyclanilide, 4-methyl-benzinidazolone, chlorohexidine, and hexachlorophene, and wherein the carrier is a member selected from the group consisting of fabrics, plastic fibers, porous foam rubber and paper.

2. The therapeutic preparation for topical application according to claim 1, wherein the carrier is a member selected from the group consisting of double knit polyester, polyester fiber, polyolefin fiber, cotton gauze, double selvage edged gauze, surgical linen, bleached cotton percale, polyamide fabric and cellulosic fabrics.

3. The therapeutic preparation for topical application according to claim 1, wherein the carrier is a double knit polyester fabric, the polymer is poly(2,2-dioxohexamethylene tetrahydrofuran) and the chemotherapeutic is 4-homosulfanilamide.

4. The therapeutic preparation for topical application according to claim 3, wherein the fabric contains 4 grams of poly(2,2-dioxohexamethylene tetrahydrofuran) and the polymer has mixed therein 0.1 to 30% by weight of 4-homosulfanilamide.

5. The therapeutic preparation for topical application according to claim 1, wherein the composition additionally contains an antibiotic agent that is a member selected from the group consisting of bacitracin, zinc bacitracin, chlortetracycline monohydrochloride, colistin sulfate, cycloserin, erythromycin, chloramphenicol, gentamicin sulfate, neomycin sulfate, polymyxin sulfate, ampicillin, sodium cephalothin, penicillin and lincomycin.

6. The therapeutic preparation for topical application according to claim 1, wherein the composition additionally contains an enzyme that is a member selected from the group consisting essentially of papain, trypsin, collagenase, subitilisin, pepsin, lysozyme, streptokinase and fibrinolysin.

* * * * *